(12) United States Patent
Valentino et al.

(10) Patent No.: US 10,272,216 B2
(45) Date of Patent: Apr. 30, 2019

(54) NEBULIZER

(71) Applicants: Alejandro Valentino, Berazategui (AR); Miriam Noemi Antelo, Berazategui (AR)

(72) Inventors: Alejandro Valentino, Berazategui (AR); Miriam Noemi Antelo, Berazategui (AR)

( * ) Notice: Subject to any disclaimer, the term of this patent is extended or adjusted under 35 U.S.C. 154(b) by 341 days.

(21) Appl. No.: 15/392,711

(22) Filed: Dec. 28, 2016

(65) Prior Publication Data
US 2017/0361039 A1    Dec. 21, 2017

(51) Int. Cl.
| A61M 15/00 | (2006.01) |
| A61M 11/00 | (2006.01) |
| A41G 7/00  | (2006.01) |
| A61M 16/06 | (2006.01) |
| A61M 16/08 | (2006.01) |

(52) U.S. Cl.
CPC .......... *A61M 15/0085* (2013.01); *A41G 7/00* (2013.01); *A61M 11/005* (2013.01); *A61M 16/06* (2013.01); *A61M 16/0816* (2013.01); *A61M 16/0683* (2013.01); *A61M 2205/59* (2013.01); *A61M 2205/8206* (2013.01)

(58) Field of Classification Search
CPC .......... A61M 15/0085; A61M 16/0816; A61M 16/06; A61M 11/005; A61M 2205/8206; A61M 16/0683; A61M 2205/59; A41G 7/00
See application file for complete search history.

(56) References Cited

U.S. PATENT DOCUMENTS

| 2005/0092325 A1* | 5/2005 | Dionne ................ A61M 16/08 128/205.25 |
| 2009/0130942 A1* | 5/2009 | Post ........................ A41G 7/00 446/27 |
| 2009/0250064 A1* | 10/2009 | Strawder ............... A61M 16/06 128/207.11 |

\* cited by examiner

*Primary Examiner* — Amber R Stiles
(74) *Attorney, Agent, or Firm* — Law Offices of Michael L. Wise, LLC

(57) ABSTRACT

It is a support mask with a mounting strip to the head of the user. Inside the mask, the actuating mask is fixed with its vapor inlet tube connected, removable, with the injector tube of an external receptacle where a micro compact removable nebulizer is set up. The micro nebulizer has a micro ultrasonic cavitation microsystem capable of generating the vibrations necessary to vaporize the medicated liquid contained in a built-up tank. That ultrasonic mechanism is activated by a small electronic device with an activation button that is housed in a side enclosed area and is powered by batteries inside a similar battery enclosed area on the opposite side. The external surface of said support mask, presents, in strategic places, fixation means to enable an external party face mask of a laminar material molded similar to those characters admired by children.

6 Claims, 2 Drawing Sheets

NEBULIZER

Figure 1:
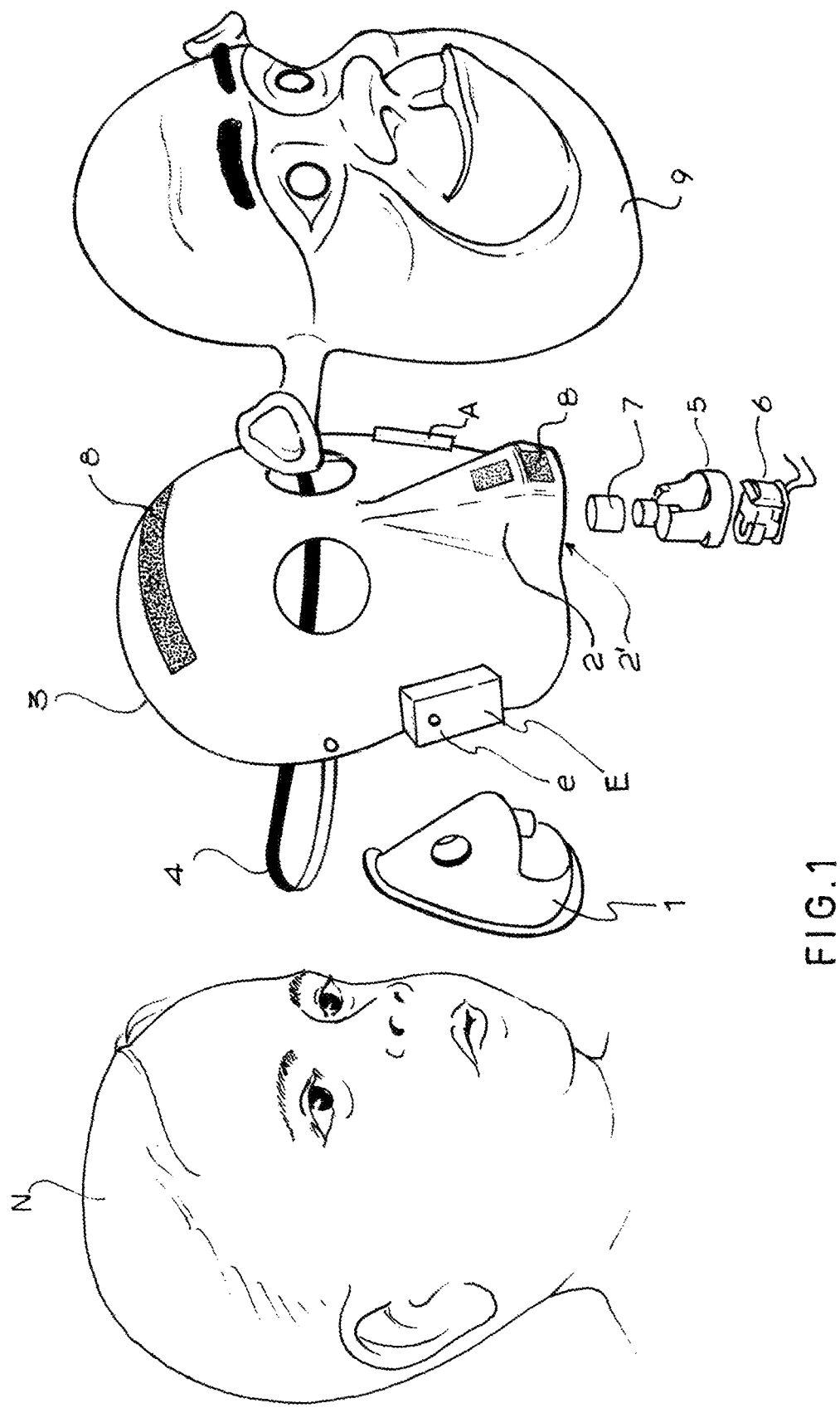
Figure 2:
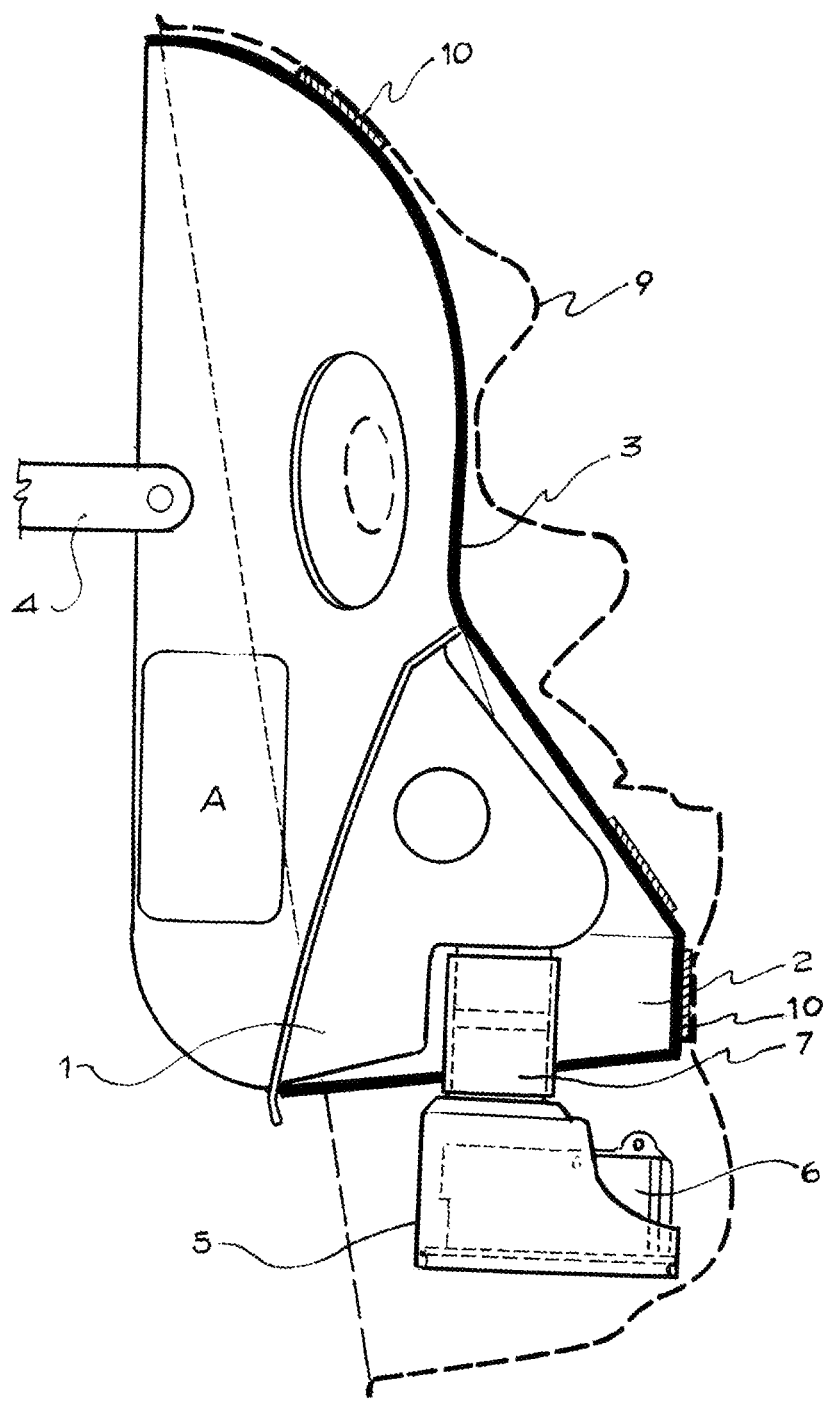

The herein utility model application is referred to a NEBULIZER that can be used mainly in pediatric treatments to carry out the nebulization process by avoiding the usual resistance of children to hold the mask to the face and by solving the inconvenience caused by their natural movement during the practice period, preventing their Operational linkage with conventional equipment.

Specifically, it is a support mask with a mounting strip to the head of the user. Inside the mask, the actuating mask is fixed inside with its vapor inlet tube connected, removable, with the injector tube of an external receptacle where a micro compact removable nebulizer is set up. The micro nebulizer has a micro ultrasonic cavitation microsystem capable of generating the vibrations necessary to vaporize the medicated liquid contained in a built-up tank. That ultrasonic mechanism is activated by a small electronic device with an activation button that is housed in a side enclosed area and is powered by batteries inside a similar battery enclosed area on the opposite side. The external surface of said support mask, presents, in strategic places, fixation means to enable an external party face mask of a laminar material to be molded similarly to those characters admired by children.

Both the mask and the external socket are easily removable to enable its cleaning and the micro nebulizer is extracted from this socket to carry out its liquid filling.

To carry out the nebulization, the mask is fixed to the support mask through its coupling with the socket provided with the micro nebulizer with its deposit filled with the medicated liquid to be evaporated. The support mask is placed with the help of the mounting strip; the external mask is applied which will be accepted by the child since he will be able to move due to the autonomy of the nebulizer free of cables and tubes, with the cooperating action of the electronic device that will provoke the detection of the device once the dose of liquid is consumed, allowing the child to continue playing without the need to remove the mask.

SCOPE OF THE INVENTION

The aforementioned nebulizer is applicable to the vapored treatment of the respiratory tracks in children whose natural mobility and resistance to the use of masks turn out to be a serious problem for the use of conventional nebulizer equipment. Its use is extended to older patients with regressive pathologies.

STATE-OF-THE-ART

The state-of-the-art nebulizer equipment have an ultrasonic vaporizer device which must remain static due to its linkage to the electric network and a mask attached to said device through tubes that prevents the mobility of the patient. Their lack of autonomy and the resistance to the use of the mask make them little suitable for pediatric use.

PURPOSE OF THE UTILITY MODEL

Therefore, it is the main purpose of this Utility Model to provide an autonomous nebulizer that allows the user to move during the treatment and also, through the use of selectively applied party face masks, that turns out to be an entertainment that avoids children from bothering using the mask.

The Nebulizer which motivates the present application is a new form applied to the known nebulizers, which implies a better use in the function to which they are destined, which confers it the category of Utility Model.

In order to realize the functional and constructive characteristics of the Reference Utility Model, a preferred example of development is illustrated below, schematically illustrated and without a specific scale in the accompanying drawing sheets, with the express clarification that precisely because it is an example, it is not suitable to assign a limitative nature to it, but it simply has a merely illustrative intention of the basic conception on which it is based.

DESCRIPTION OF THE FIGURES

FIG. 1 is a perspective view of the nebulizer shown in front of a child's face.

FIG. 2 is a cross-sectional view through a central vertical plane of the support mask and of the outer mask, showing the mask and the receptacle carrier of the micro-nebulizer.

DESCRIPTION OF THE INVENTION

As it is shown in FIG. 1, the nebulizer mask is in the frontal projection of the child's respiratory tract (N). The nebulizer mask (1) shall be placed in cavity (2) of the support face mask (3) with a mounting strip (4). The said nebulizer mask (1) is fixed securely and fitted together with the external receptacle (5) containing the compact micro nebulizer (6) by means of the coupling tube (7) that tightly passes through a hole in the bottom (2) of said cavity (2). Externally, the support face mask (3) has fastening means (8), in this example a Velcro-like fastener, for removably fixing a party face mask (9) provided with complementary fastening means.

On one side of the support face mask, the electronic device (E) is located, with power button (e), which controls the activity of the micro nebulizer whose power source (A) is located on the opposite side.

In the cut that illustrates FIG. 2, we can see the manner in which the nebulizer mask (1) positioned in the cavity (2) of the support face mask (3) is fixed securely thereto by means of the coupling tube (7) that tightly-passes through a hole in the bottom (2') to which the injector peak (5') of the receptacle (5) containing the micro-nebulizer (6) is connected. The party face mask (9) is fixed to the support face mask (3) by means of the fixing means (10).

In the lateral enclosed area (A) the batteries that feed the electronic device commanding the operation of the electronic device (E) are laid down.

The described and exemplified nebulizer falls within the scope of protection of the present Utility Model application, which is basically established by the text of the following claim list.

The invention claimed is:

1. A nebulizer of a type used for treatment of respiratory tracts by means of vaporizing of a medicament solution through an ultrasonic device, comprising:

(a) a nebulizer mask placed in a frontal cavity of an area corresponding to an entrance of said respiratory tracts of a support face mask having an operative mounting strip;

(b) said nebulizer mask is fixed securely and fitted together with an external receptacle containing a compact micro nebulizer by means of a coupling tube that tightly passes through a hole in a bottom of said cavity; and (c) externally said support face mask has a fastening means for removably fixing a party face mask provided with a complementary fastening means.

2. A nebulizer as claimed in claim 1, further having on one side of said support face mask an electronic device having a power button which controls an activity of said micro nebulizer having a power source located on an opposite side of said support face mask.

3. A nebulizer of a type used for treatment of respiratory tracts by means of vaporizing of a medicament solution through an ultrasonic device, comprising:

(a) a nebulizer mask placed in a frontal cavity of an area corresponding to an entrance of said respiratory tracts of a support face mask said support face mask has an operative mounting strip to secure said support face mask around a child's respiratory tract; and (b) said nebulizer mask is fixed securely and fitted together with an external receptacle containing a compact micro nebulizer by means of a coupling tube that tightly passes through a hole in a bottom of said frontal cavity.

4. A nebulizer as claimed in claim 3, wherein said support face mask has a fastening means on an external surface for removably securing a party face mask having a complementary fastening means on its internal surface.

5. A nebulizer as claimed in claim 4, wherein said fastening means and said complementary fastening means are a hook and loop fastening means.

6. A nebulizer as claimed in claim 3, further having on one side of said support face mask an electronic device having a power button which controls an activity of said micro nebulizer having a power source located on an opposite side of said support face mask (3).

* * * * *